United States Patent [19]

Harrow et al.

[11] 4,006,977
[45] Feb. 8, 1977

[54] PHASE CONTROL SYSTEM FOR POLARIZED SYNCHRONOUS MOTORS

[75] Inventors: Charles Lawrence Harrow, Baltimore; Jean Claude Bonnace, Kensington; Gunter Gerd Wilkens, Baltimore, all of Md.

[73] Assignee: CGR Medical Corporation, Baltimore, Md.

[22] Filed: Jan. 22, 1976

[21] Appl. No.: 651,258

[52] U.S. Cl. ............................. 352/133; 318/102
[51] Int. Cl.[2] ...................................... G03B 19/18
[58] Field of Search ............... 352/133, 85, 89, 68; 318/102; 250/313, 314, 320

[56] References Cited
UNITED STATES PATENTS

| | | | |
|---|---|---|---|
| 1,450,339 | 4/1923 | Smith | 318/102 |
| 1,980,806 | 11/1934 | Koenekamp | 352/89 |
| 2,433,129 | 12/1947 | Land | 250/320 |
| 2,586,392 | 2/1952 | Sheldon | 250/320 |

*Primary Examiner*—Monroe H. Hayes
*Attorney, Agent, or Firm*—Brady, O'Boyle & Gates

[57] ABSTRACT

A shutter phase lock circuit for a pair of biplane cine-cameras having multiframe speeds utilized in a diagnostic X-ray system wherein the cameras are driven by polarized synchronous motors. Each of the cameras have a rotating shutter which is mechanically coupled to a commutator which has a 50% duty cycle and produces a square wave output pulse. The pulses are compared provided that the same camera speed has been selected for both cameras and in the event that two pulses are out of phase by a predetermined phase angle taking into account compensation for mechanical errors, causes an error signal pulse to be produced whose pulse width is a function of the camera speed selected. The error signal pulse is phase locked to the AC line frequency and applied to a control circuit which is adapted to block the AC line voltage applied to one of the camera drive motors (slave) for a time equal to the pulse width of the error signal so as to effect slipping of the slave camera drive motor in repetitive sequences until phase synchronism of both commutator outputs occur.

14 Claims, 4 Drawing Figures

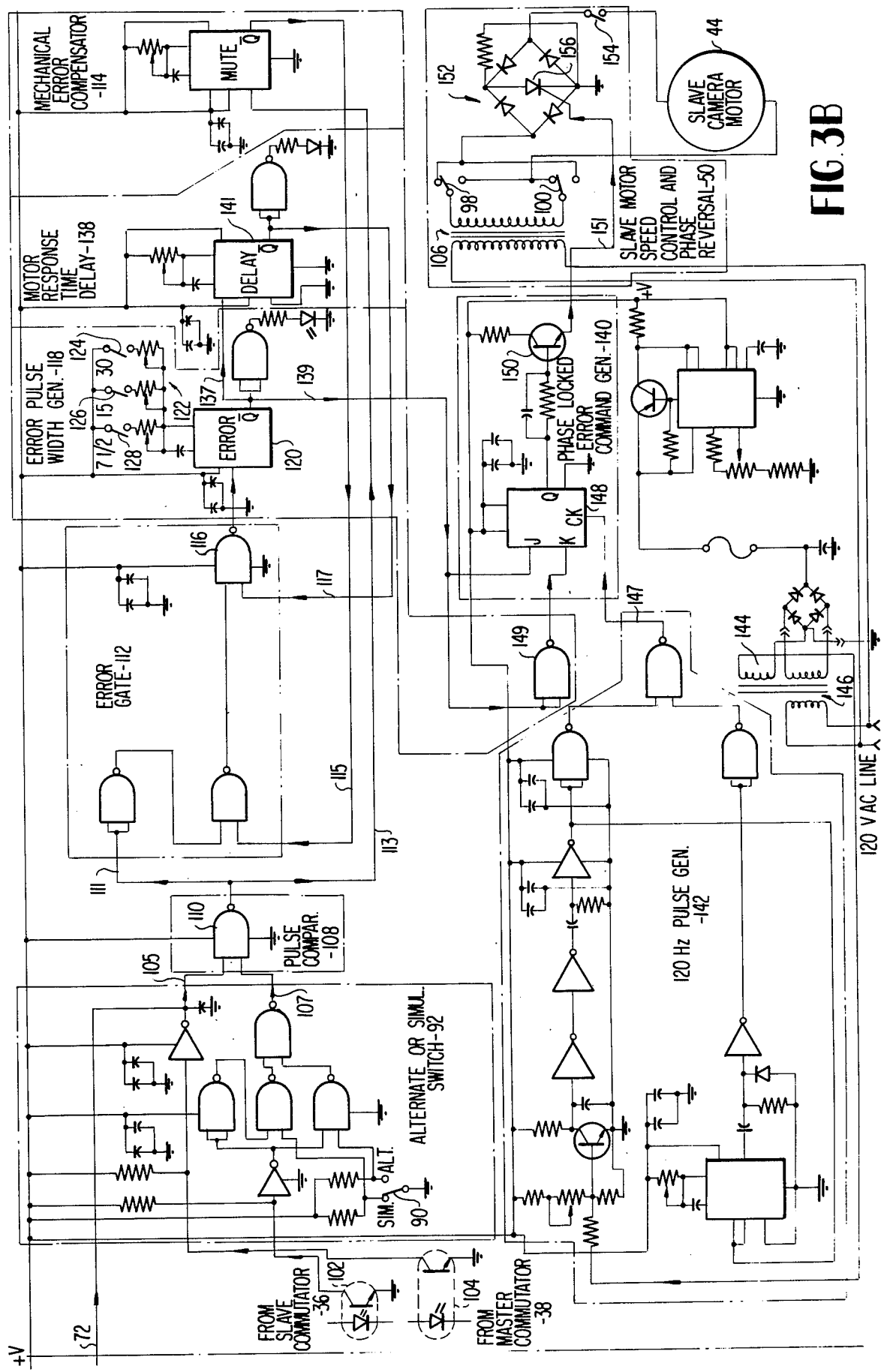

PHASE CONTROL SYSTEM FOR POLARIZED SYNCHRONOUS MOTORS

BACKGROUND OF THE INVENTION

1. Field of the Invention

This invention relates generally to X-ray apparatus and more particularly to apparatus for use in cinefluorography employing a pair of motion picture cameras and image intensifier tubes adapted for biplane operation.

2. Description of the Prior Art

If two orthogonal X-ray beams are directed toward their respective receivers simultaneously, whether by accident or by design, the object being radiated by X-rays tends to scatter radiation omni-directionally, resulting in radiation directed to one receiver being diverted to and causing fogging at the other receiver situated in the orthogonal plane. By providing means to synchronize the position of the cinecamera shutters in such a way that if one shutter is open while the other is closed, and vice versa, two desired effects are obtained. First, since the opening of the shutter normally triggers the X-ray exposure, the exposures are produced alternately in two orthogonal planes. Secondly, since the X-ray exposure and open shutter are coincidental only in the same plane, the problem of cross scattered radiation is diminished, if not eliminated.

X-ray cine biplane operation is a well known technique. Where a single frame speed e.g. 60 frames per second (fps) is utilized, synchronous AC motors can be utilized to drive the cameras; however, synchronous motors, particularly polarized synchronous motors, are not readily adaptable to synchronous speed control where multispeed operation of the cameras is desired. In such applications, synchronized DC motors are normally utilized.

SUMMARY

Briefly, the subject invention is directed to a shutter phase lock circuit including a pair of polarized AC synchronous motors driving respective cinecameras for use in cinefluorography and wherein a master camera commutator and a slave camera commutator each generate a 50% duty cycle output signal which is compared in phase in a pulse comparator which is enabled by a signal generated in the event that both the master and slave camera has been activated and are selectively operated at a same multispeed frame rate other than that equal to line frequency. If the phase comparison varies by a predetermined amount taking into account mechanical error compensation, an error pulse width generator is triggered to provide an output pulse having a variable pulse width which is a function of the selected camera speed, and thus a pulse width modulated error signal is provided. The error signal is phase locked to the AC line voltage and fed to a control circuit coupled to the slave camera motor which is operable to block application of the AC line voltage thereto for a time equal to the pulse width of the error signal and thus slip the slave camera drive motor by a predetermined amount. Once the error pulse width generator has been triggered, further triggering is inhibited while the instant correction is made. If an error still exists, the corrective sequence described above is repeated. If no error exists, no additional sequence is initiated. Furthermore, for single plane operation or biplane operation at a camera speed of 60 frames per second, the circuitry comprising the subject invention is rendered inoperative.

BRIEF DESCRIPTION OF THE DRAWINGS

FIGS. 3A and 3B disclose schematically the specific electrical circuitry included in the various portions of the block diagram shown in FIG. 2.

DESCRIPTION OF THE PREFERRED EMBODIMENT

The purpose of the present invention is to operate the shutters of two biplane cinefluoroscopic cameras in a biplane mode either 180° out of phase or in phase to provide alternate or simultaneous exposures respectively, for cameras having a plurality of selective frame speeds e.g. 60, 30, 15 and 7½ frames per second (fps).

Figure 1:
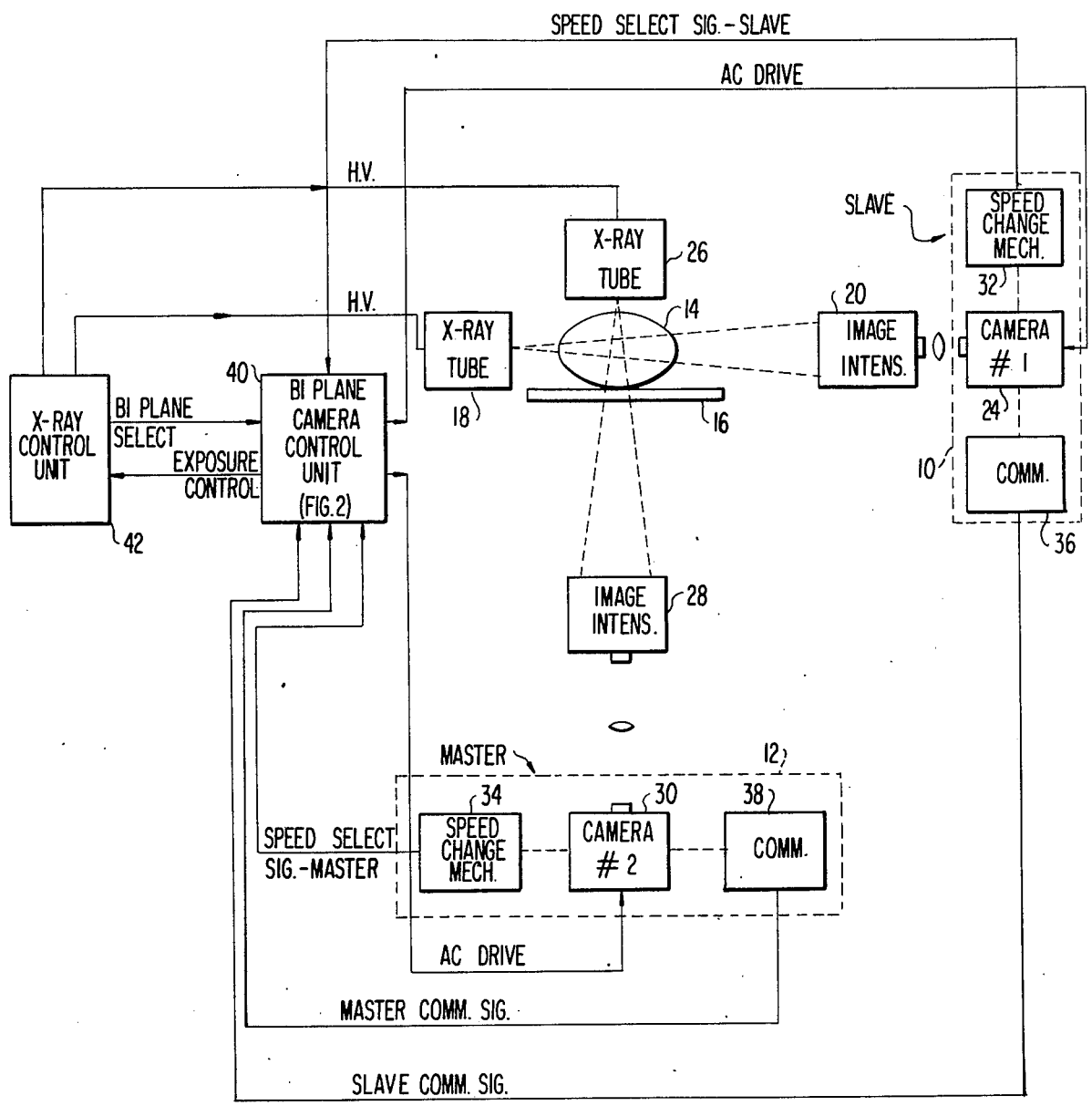
FIG. 1 is a system block diagram generally illustrative of the subject invention.

Referring now to FIG. 1, reference numerals 10 and 12 designate a pair of biplane cine camera assemblies which are adapted to record X-ray images taken through mutually perpendicular axes through an object 14 which may be, for example, a patient positioned on an X-ray table 16. A first X-ray tube 18 is adapted to pass a beam through the object 14 along a first or lateral (LAT) orthogonal axis where it is directed to an image intensifier tube 20 whose output is optically coupled to a first or slave camera 24. A second X-ray tube 26 is adapted to make X-ray exposures vertically or along the anterior position (AP) axis through the body 14 which in combination with a second image intensifier tube 28 produces an X-ray image which is optically coupled to a second or master cine camera 30.

Both the slave and master cameras 24 and 30 each have a respective speed change mechanism 32 and 34 including selector switches, not shown, which permits a plurality of frame rates or speeds to be made individually for each camera. Each of the cameras furthermore are respectively mechanically coupled to electrical commutators 36 and 38 which are adapted to operate synchronously with a rotating camera shutter, not shown, which operate at a 50% duty cycle. As such, the commutators 36 and 38 generate square wave type electrical signals which are applied to a biplane camera control unit 40 which is the subject of the subject invention and is shown in detail by the block diagram illustrated in FIG. 2 and by the electrical schematic diagram shown in FIGS. 3A and 3B.

In operation, the control unit 40 is adapted to trigger the application of high voltage to the X-ray tubes 18 and 26 from an X-ray control unit 42 in synchronism with the operation of the biplane cameras 24 and 30. Briefly, in operation the biplane control unit 40 is only operative for biplane operation at a camera speed other than that equal to the AC line frequency which in the U.S.A. is 60Hz. Accordingly, the biplane mode of operation is adapted to be selected at the X-ray control unit 42 which closes switch means, not shown, in the camera the control unit 40 which additionally receives respective speed selection information from the speed change mechanisms 32 and 34 via the selection switches, which if the same camera speed is selected at both cameras, permits or enables the camera control unit to apply AC drive potentials to the cameras 24 and 30. Each camera shutter, not shown, is mechanically linked to respective electrical commutator means 36 and 38 which provide an electrical square wave output signal whose repetition rate follows that of the respective shutter. The biplane camera control unit 40 compares the output phase of the slave camera commutator 36 to the output of the master camera commutator 38 and in accordance therewith controls the application of the AC drive to the slave camera 24, in a manner to be described, until the two polarized synchronous motors driving the cameras 24 and 30 and accordingly the camera shutters are locked in phase for the camera speed selected by the operator.

Figure 2:
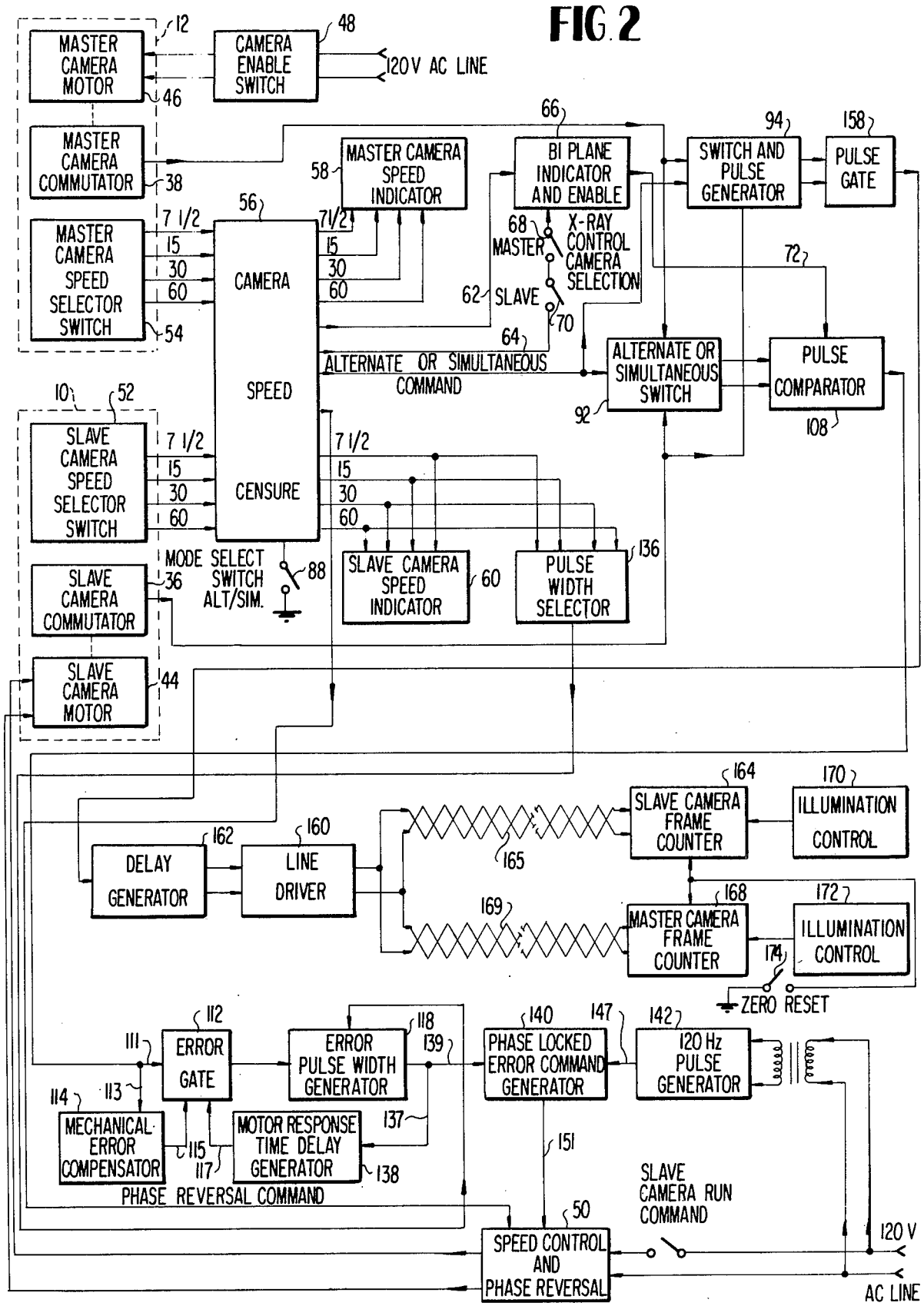
FIG. 2 is a detailed block diagram illustrative of the preferred embodiment of the subject invention.
Figure 3A:
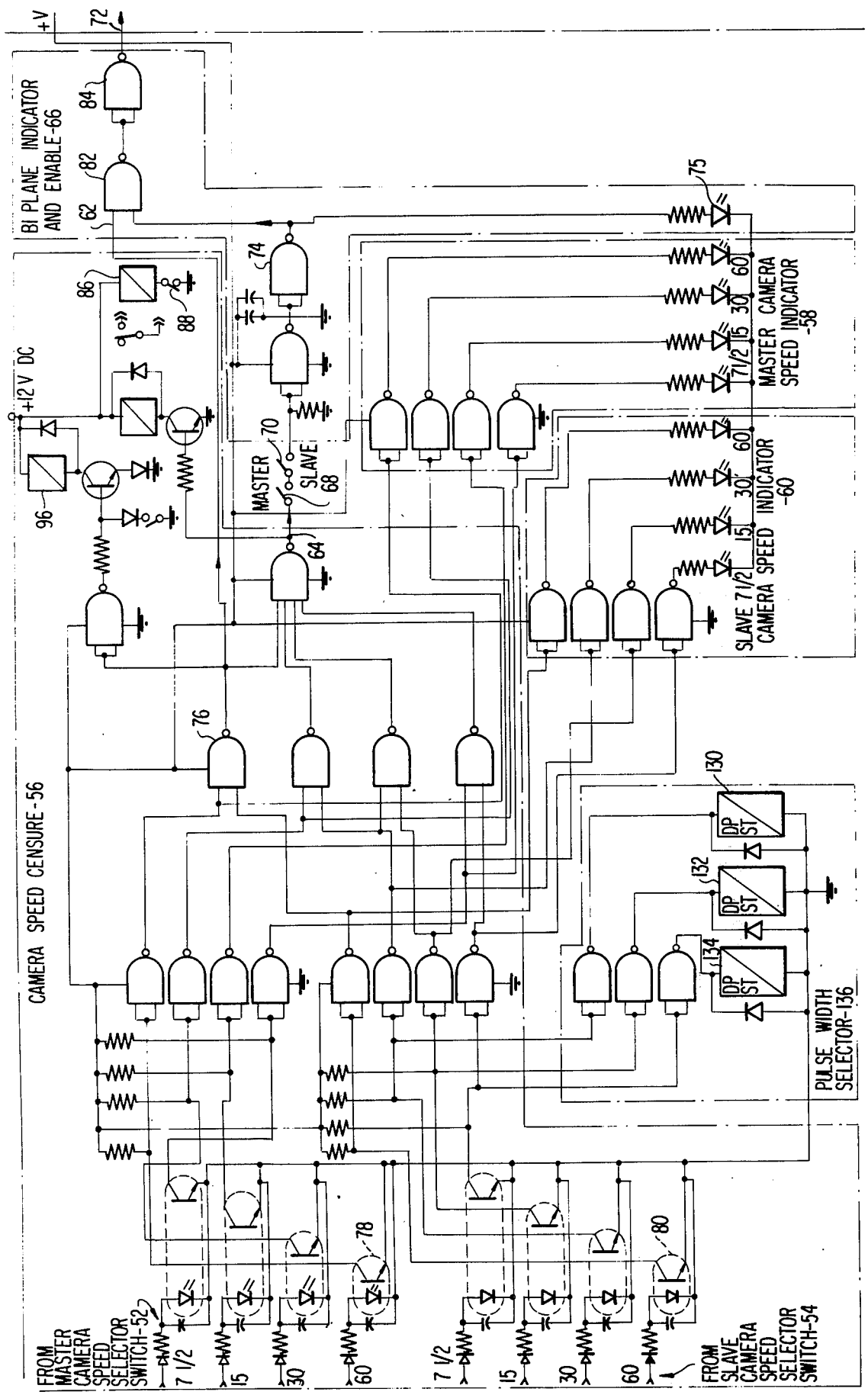

Considering now the biplane camera control unit 40 in greater detail, reference is now made jointly to FIG. 2 and FIGS. 3A and 3B wherein reference numeral 44 (FIG. 2) designates a polarized AC synchronous motor utilized to drive the slave camera 24 shown in FIG. 1, and reference numeral 46 designates a second polarized AC synchronous motor utilized to drive the master camera 30. The master camera motor 46 is coupled to the AC line voltage by means of a master camera enable switching unit 48 so that the line voltage is continuously applied when operation of the master camera 30 is desired. The slave camera motor 44, however, is coupled to the AC line voltage through a speed control and phase reversal circuit 50, shown in detail in FIG. 3B, whose operation is to selectively block the application of the AC line voltage applied to the slave motor 44 in order to phase lock the output of the slave camera commutator 36 to the output of the master camera commutator 38 and thus phase lock the shutters.

The speed change mechanisms 32 and 34 shown in FIG. 1 include a respective speed selector switch 52 and 54 which are adapted to couple signals to a camera speed censure circuit 56 for camera speeds or frame rates of 60, 30, 15 and 7½ fps. The camera speed censure circuit 56 comprises a binary logic circuit shown in detail in FIG. 3A, with the coupling to the switches 52 and 54 being achieved by photodiodes optically coupled to phototransistors. The censure circuit 56 determines which speed is selected for each camera by coupling outputs to a respective photodiode in a master camera speed indicator circuit 58 and a slave camera speed indicator circuit 60 shown in FIG. 3A. The logic circuitry of the censure circuit 56 also determines if biplane operation is possible which is when both cameras 24 and 30 have the same selected speed. If the same speed i.e. 7½, 15, 30 and 30 and 60 fps is selected, a signal is outputted on lines 62 and 64 to a biplane indicator and enable circuit 66 shown in detail in FIG. 3A. Signal line 64, however, is coupled to the circuit 66 by means of a pair of master and slave relay switch contacts 68 and 70 which are respectively closed when the master and slave cameras are turned on at the X-ray control unit 40 (FIG. 1).

In the event that relay switch contacts 68 and 70 are closed and signals appear on lines 62 and 64, a logic enable signal appears on signal line 72. Additionally, a photodiode 75 is energized by the output of the logic module 74 to indicate biplane operation. It should be pointed out that if either the master or slave camera is unenergized, one of the relay switch contacts 68 or 70 will remain in an open state whereupon no signal will appear at the output of NAND gate 74 and thus no signal will appear on circuit lead 72 and the remainder of the circuitry will remain inoperative.

It should also be pointed out that circuit lead 62 is coupled to the output of gate 76 in the censure circuit which is responsive to circuit elements 78 and 80 which are energized when 60 frames per second speed is selected. Accordingly, the output of the gate 76 provides a signal of a first logic sense for 60 fps operation and a signal of an opposite logic sense for the other speeds selected. Accordingly, the action of gates 82 and 84 only provide an enabling signal on line 72 when biplane operation is desired and a frame speed other than 60 fps is selected. The remainder of the circuitry accordingly becomes inoperative for single plane operation or 60 fps operation.

Additionally, the camera speed censure circuit 56 provides either an alternate or simultaneous biplane mode command to the system by operation of relay coil 86 (FIG. 3A) which is energized by closure of a control panel switch 88 shown both in FIG. 2 and FIG. 3A and by operation of the slave motor control and phase reversal circuit 50. A command is provided by means of a pair of relay contacts 90 included in the alternate or simultaneous electronic switch circuit 92 shown in detail in FIG. 3B and by another pair of relay contacts, not shown, included in an electronic switch and pulse generator circuit 94. Regarding the slave motor circuit 50, a phase reversal command for simultaneous biplane mode operation is coupled to the slave camera control circuit 50 from the censure circuit 56 by means of a relay including relay coil 96 (FIG. 3A) which is adapted to operate a pair of relay contacts 98 and 100 shown in FIG. 3B. These relay contacts are adapted to reverse the phase of the line potential applied to the slave camera drive motor 44.

The slave camera commutator 36 shown in FIG. 2 is coupled to a photodiode-transistor assembly 102 shown in FIG. 3B while the master camera commutator 38 is coupled to a like photodiode-transistor assembly 104. The transistor outputs of the assemblies 102 and 104 comprise 50% duty cycle square waves, which due to operation of the slave motor control circuit 50 are adapted to be in-phase for the simultaneous mode of operation, but 180° out of phase with one another for alternate biplane mode of operation. The electronic switch circuit 92 shown in detail in FIG. 3B, is adapted to buffer the square wave outputs coupled from the photodiode-transistor assemblies 102 and 104 and reverse the phase of the signal from the slave commutator 36 when simultaneous mode is selected. The reason for the signal reversal is that the outputs of the switch circuit 92 appearing on lines 105 and 107 are coupled to the pulse comparator 108 which requires two signals opposite in phase 180° for its operation.

The pulse comparator circuit 108 is comprised of a NAND circuit module 110 which provides an output when the two input signals applied thereto are not exactly 180° out of phase and therefore, do not cancel one another. An output is accordingly provided whose pulse width is proportional to the difference in phase from 180°. The leading edge of this output, if any, is applied via signal line 111 to an error gate circuit 112 shown in detail in FIG. 3B, and to a signal pulse generator 114 via signal line 113 which is adapted to produce a pulse of predetermined fixed pulse width which is applied as an inhibiting or muting signal back to the error gate 112 via signal line 115 to compensate for minor differences in the master and slave commutators caused by inherent mechanical errors in the devices themselves.

If, for example, the output from the pulse comparator 108 is greater in pulse width than the pulse width from the mechanical error compensator pulse generator 114, an output will appear at the output of the gate 116. The leading edge of this signal triggers an error pulse width generator circuit 118 including a solid state module 120 configured as a one-shot multivibrator, whose output pulse width at the Q terminal is determined by a plurality of RC time constant networks 122 which are selectively switched into operation in accordance with closure of relay circuit contacts 124, 126 and 128 for frame speeds of 30, 15 and 7½ fps, respectively, in accordance with operation of respective relays whose relay coils 130, 132 and 134, are included in a pulse selector circuit 136 shown in detail in FIG. 3A and which is controlled by the camera speed censure circuit 56.

Thus in accordance with the frame speed selected, an output from the pulse comparator circuit 108 greater in pulse width than the pulse width of the mechanical error compensator circuit 114 causes the error gate 112 output to trigger pulse generator 118 whereupon an error signal pulse of one of three predetermined pulse widths is generated which appears at the Q output of the logic module 120. This signal is coupled to a time delay generator circuit 138 which is shown in detail in FIG. 3B via signal lead 137 and a phase locked error command generator circuit 140 which is also shown in detail in FIG. 3B via signal lead 139. The time delay generator circuit 138 includes a one-shot multivibrator logic module 141 which becomes operative by the output of the error pulse width generator 118 to generate a pulse at its Q output to inhibit or mute the error gate circuit 112 via signal lead 117 for a time at least equal to the pulse width appearing at the Q output of the module 120.

The phase locked error command generator circuit 140 in addition to being coupled to the output of the error pulse width generator 118 by means of circuit lead 139 is fed to the output of a 120Hz pulse generator 142, shown in detail in FIG. 3B. This circuit is driven by the secondary winding 144 of a transformer 146 whose primary winding is coupled to the 60Hz line potential, as shown in FIG. 3B. The 120Hz output of the pulse generator circuit 142 appearing on circuit lead 147 is adapted to clock a J-K flip-flop circuit 148 and thus phase lock the output of the error pulse width generator 118 which is applied at the J and K inputs be means of logic gate 149 and circuit lead 139. The Q output of the flip-flop 148 thus comprises a phase locked pulse width modulated signal which is applied by means of transistor 150 and signal lead 151 to an SCR controlled diode bridge network 152 coupled to the slave motor 44 via a slave camera run command switch 154.

Accordingly when an error signal from the error pulse width generator circuit 118 is applied to the phase locked error command generator 140, the signal applied to the gate of the SCR 156 starts and stops at precise points on the AC line frequency for a time equal to the pulse width of the error signal. As a consequence the actual corrected signal is phase locked to the AC line potential appearing across the primary winding of transformer 146.

Speed control is thus achieved by removing the AC line potential from the slave camera motor 44 for precise time intervals governed by the three predetermined pulse widths which are generated by the error pulse width generator 118, depending upon the selected camera frame speed of 30, 15 and 7½ fps. After a corrective signal has been applied, the time delay generator 138 will then allow the error gate 112 to again become operable which if an error still exists at the output of the pulse comparator 108 which is greater than the pulse width of the mechanical error compensator circuit 114, causes the error pulse width generator 118 to again be triggered and a corrective action repeated. If no error exists which is greater than the pulse width output from the mechanical error compensator circuit 114, no further action is initiated.

As indicated earlier in this specification, when 60 fps biplane mode is selected, the biplane enable circuit 66 is disabled since the polarized synchronous motors 44 and 46 for the slave and master cameras will automatically phase lock when operated at the line frequency which is 60Hz. It is only when camera speeds less than 60 fps are selected that the corrective servo loop comprising the subject invention is set into operation.

In addition, film frame counter circuitry is disclosed in FIG. 2 which is responsive to the operation of the slave and master camera commutators 36 and 38 as provided by the respective square wave outputs of the photodiode-transistor assemblies 102 and 104. The two square wave signals are fed to the pulse generator circuit 94 providing respective pulses therefrom which are combined in a pulse gate circuit 158 in accordance with whether alternate or simultaneous mode is selected. A line driver circuit 160 is coupled to the pulse gate 158 through a time delay generator 162. The output of the line driver circuit 160 is coupled to a first frame counter 164 for the slave camera through a twisted lead pair 165 and to a second or master camera frame counter 168 through the twisted lead pair 169. The action of the time delay generator 162 provides a short time delay so that the numerical indications of the frame counters 164 and 168 do not appear until the respective camera shutters have opened. Both frame counters 164 and 168 have illumination control circuits 170 and 172 coupled thereto and a reset switch 174 is also provided to provide a zero reset at the end of or prior to any operational sequence.

Having thus shown and described what is at present considered to be the preferred embodiment of the subject invention,

We claim:

1. A system for phase locking the shutters of two cinefluorographic cameras arranged along two mutually perpendicular axes and having selective multiple frame speeds, and which are adapted to be operated singly in a mono-plane mode or in combination in a biplane mode, alternately or simultaneously, said cameras being driven by respective synchronous drive motors, the improvement comprising in combination:

respective circuit means applying an AC potential of a predetermined frequency to each of said synchronous drive motors;

means coupled to said shutters providing respective electrical output signals in response to the open and closed state of said shutters;

circuit means coupled to said respective electrical output signals and being operative to compare the phase of said electrical signals for a common frame speed of said cameras to provide a pulse output signal for a predetermined phase difference between said electrical output signals;

signal generator means coupled to said pulse output signal and being triggered thereby to provide a pulse output signal of a predetermined different pulse width for each frame speed of said cameras; and circuit means phase locking said pulse output signal of predetermined pulse width to said AC potential and applying said phase locked pulse output signal to said respective circuit means applying said AC potential to one of said synchronous drive motors whereby said AC potential is removed from said one synchronous drive motor for a time period substantially equal to the pulse width of said pulse output signal of predetermined pulse width causing said one synchronous drive motor to slip relative to the other synchronous drive motor to achieve proper phasing therebetween.

2. The system as defined by claim 1 wherein said synchronous motor is comprised of polarized synchronous motors and wherein said AC potential of a predetermined frequency comprises the AC line potential.

3. The system as defined in claim 1 wherein said common frame speed is a sub-multiple of the AC potential frequency applied to said drive motors.

4. The system as defined by claim 1 wherein the selective multiple frame speed of said cameras is equal to m/n wherein m is equal to the AC line potential frequency, and n is equal to an even numbered integer.

5. In diagnostic X-ray apparatus, a system for synchronizing the shutters of a pair of cine cameras arranged for and providing a biplane mode of operation either alternately or simultaneously, said cameras having selective multiple frame rates and being driven by respective polarized synchronous motors, comprising in combination:

respective circuit means adapted to apply an AC line potential of predetermined frequency to said synchronous drive motors;

means coupled to said shutters to provide respective electrical signals in response to the open and closed state of said shutters at each of said frame rates;

circuit means responsive to the selected frame rate of said two cameras providing an enabling signal for said biplane mode of operation when both cameras have the same selected frame rate other than the frequency of said AC line potential;

circuit means coupled to said respective electrical signals and being coupled to and responsive to said enabling signal and becoming operative thereby for comparing the phase of said respective electrical signals to provide an output signal for a phase difference of a predetermined magnitude;

signal generator means coupled to said circuit means providing said output signal and being triggered thereby to provide a pulse output signal of a predetermined pulse width determined by the same selected frame rate of the two cameras; and circuit means phase locking said pulse output signal of predetermined pulse width to said AC line potential and applying the phase locked pulse output signal to said respective circuit means applying said AC line potential to one of said polarized synchronous motors whereby said AC line potential is removed from said one motor for a period substantially equal to the predetermined pulse width of said output signal causing said one motor to slip relative to the other motor to achieve proper phasing therebetween and thereby phase lock said shutters.

6. The system as defined by claim 5, wherein said cameras additionally include speed selector means coupled thereto and, wherein said means providing said enabling signal includes a camera speed censure circuit coupled to said camera speed selector means for providing an output control signal when the same frame rate other than a frame rate equal to the frequency of said AC line potential has been selected for both cameras, and an enabling circuit coupled to said output control signal and a signal coupled thereto indicating that biplane mode of operation is desired wherein both cameras are utilized and being operable in response to the last two recited signals to generate said enabling signal.

7. The system as defined by claim 5, wherein said circuit means for comparing is adapted to compare electrical signals which are in the order of 180° out of phase with one another, and wherein said circuit means applying said AC line potential to said one synchronous motor is adapted to provide a like phase of said AC line potential to said one synchronous motor relative to the AC line potential applied to the other motor during simultaneous biplane operation and a phase reversal of said line potential to said one synchronous motor for alternate biplane operation, and additionally including selectively operated phase reversal circuit means coupled between said respective electrical signals to said circuit means for comparing and being adapted to invert the phase of one of said electrical signals for simultaneous biplane operation.

8. The system as defined by claim 5 wherein said circuit means for comparing additionally includes a signal generator actuable in response to said output signal to provide a fixed pulse width signal adapted to allow for mechanical errors in said means coupled to said shutters, and gating circuit means coupled to said output signal and said fixed pulse width signal and providing an output trigger signal when the phase difference between said output signal and said fixed pulse width signal is of a period greater than the pulse width of said fixed pulse width signal whereby said signal generator means is triggered only when the phase difference of said electrical signals exceeds a predetermined mechanical tolerance of said commutations.

9. The system as defined by claim 8 and additionally including a motor response time delay generator circuit coupled to and responsive to said pulse output signal of said signal generator means and being operable to generate a signal coupled to said gating circuit means for rendering said gating circuit means inoperative for a period substantially equal to or greater than the pulse width of said pulse output signal to prevent further triggering of said signal generator means until the instant phasing correction is completed.

10. The system as defined by claim 5 and additionally including pulse width selector means having selective control circuit means coupled to said signal generator means and being actuated in accordance with the selected frame rate of said cameras to control the pulse width of said pulse output signal of predetermined pulse width from said signal generator means.

11. The system as defined by claim 5 and additionally including pulse generator means operated in response to said AC line potential applied thereto and generating a phase locking pulse signal of twice the line potential frequency coupled to said circuit means phase locking said pulse output signal to said AC line potential.

12. The system as defined by claim 5 wherein said means coupled to said shutters comprise respective electrical commutators adapted to provide electrical output signals having respective waveforms with the same duty cycle as said shutters.

13. The system as defined by claim 12 and additionally including frame counters for each of said cameras and additionally including circuit means coupled to said commutators for operating said frame counters.

14. The system as defined by claim 13 wherein said circuit means operating said frame counters includes pulse generator means responsive to each commutator to provide a pulse for the respective frame counter and additionally including time delay circuit means coupled between said pulse generator and said frame counters to provide a short time delay so that numerical indications on the respective frame counters will not appear until the respective camera shutters have opened.

* * * * *